United States Patent [19]

Sloane

[11] 4,359,415
[45] Nov. 16, 1982

[54] ISOLATION OF AN ANTINEOPLASTIC PROTEIN FRACTION AND AN ANTINEOPLASTIC PEPTIDE FRACTION FROM HUMAN URINE

[75] Inventor: Nathan H. Sloane, Germantown, Tenn.

[73] Assignee: University of Tennessee Research Corporation, Knoxville, Tenn.

[21] Appl. No.: 269,995

[22] Filed: Jun. 3, 1981

[51] Int. Cl.³ .............................................. C07G 7/00
[52] U.S. Cl. ................................. 260/112 R; 424/99; 424/177
[58] Field of Search .............. 260/112 R; 424/99, 177

[56] References Cited

U.S. PATENT DOCUMENTS 3,711,377  11/1973  Sloane ............................. 195/66 B

OTHER PUBLICATIONS

Chem Abs. 71:20387a.
Burzynski Physiol. Chem. & Physics pp. 457–468, 6(1974).
Burzynski et al. Physiol. Chem. & Physics pp. 13–22, 8(1976).
Burzynski Physiol. Chem. & Physics pp. 275–279, 8(1976).
Burzynski Physiol. Chem. & Physics pp. 437–447, 5(1973).

*Primary Examiner*—Allan Lieberman
*Assistant Examiner*—P. Short
*Attorney, Agent, or Firm*—Luedeka, Fitch & Neely

[57] ABSTRACT

The passage of human urine through a bed of adsorbent material results in the adsorption from the urine of antineoplastic substances as determined by in vitro tissue culture techniques utilizing human tumor cells. The adsorbent yields two antineoplastic fractions upon sequential elution. Elution of the low-molecular weight antineoplastic fraction is accomplished by elution with cold aqueous acetone at slightly alkaline pH. Thereafter, elution of the high molecular weight antineoplastic fraction is accomplished by elution with a cold aqueous acetone-glycerol mixture at slightly alkaline pH.

The antineoplastic activities of these fractions are determined by tissue culture techniques employing a variety of human neoplastic cells. Furthermore, the high molecular weight fraction, the antineoplastic urinary protein, also inhibits the progression and causes regression of certain human tumor cells implanted in the nude mouse.

12 Claims, No Drawings

ISOLATION OF AN ANTINEOPLASTIC PROTEIN FRACTION AND AN ANTINEOPLASTIC PEPTIDE FRACTION FROM HUMAN URINE

The present invention relates to the extraction and purification of two types of antineoplastic substances that are present in human urine and to methods for the extraction and purification thereof. In particular, it relates to two types of antineoplastic fractions, a low molecular weight peptide and high molecular weight protein which are extractable from human urine by adsorption upon a synthetic magnesium silica gel and subsequent elution therefrom.

Generally, in accordance with the present invention, human urine is passed through an adsorbent bed of synthetic magnesium silicate which extracts two fractions, a peptide fraction and a protein fraction, along with several other unidentified components. The adsorbent bed is then washed with cold distilled water to remove the remaining urine. Each of the desired antineoplastic fractions, the peptide fraction and the protein fraction, is sequentially eluted from the magnesium silicate. The low molecular weight peptide fraction is first eluted with aqueous acetone at slightly alkaline pH. Thereafter, the high molecular weight protein fraction is eluted by a mixture of water, acetone and glycerol at slightly alkaline pH. The peptide fraction is concentrated in vacuo to remove acetone and the remaining aqueous solution of the peptide is further purified by membrane filtration. After dialysis to remove acetone and glycerol, the protein fraction is purified, by membrane filtration and gel filtration.

It is an object of the present invention to provide a material extractable from human urine and having significant antineoplastic activity. It is also an object to provide a method for extracting from human urine a material having significant antineoplastic activity. Various other objects and advantages will be noted when the following description is considered.

The presence of antineoplastic peptides in human urine was described by Burzynski et al in a series of publications [Physiol. Chem. Phys., 5, 436 (1973); 6, 457 (1974); 8, 13 (1976); 8, 275 (1976)]. These peptides showed antineoplastic activity against various human tumor cell lines and did not effect the growth of normal cells. These urinary peptides were prepared by 80% ethanol extraction of urine followed by free flow electrophoresis, paper chromatography and finally, preparative thin layer chromatography.

Florisil, a synthetic magnesium silicate prepared by the Floridin Company of Pittsburgh, Pennsylvania, has been used as an adsorbent for biologically active materials in human urine, as described by Sloane in U.S. Pat. Nos. 3,711,377, Jan. 16, 1973, and 3,884,760, May 20, 1975. These patents describe the adsorption of a fibrinalytic protein enzyme from human urine by Florisil and the subsequent elution of this protein enzyme from the Florisil adsorbent.

In accordance with the present invention, both an antineoplastic peptide fraction and an antineoplastic protein fraction are adsorbed from human urine by an adsorbent, such as Florisil. Each of these antineoplastic fractions is separately eluted from the Florisil. The antineoplastic peptide is eluted initially by an aqueous acetone solution at slightly alkaline pH; the antineoplastic protein is then eluted by an acetone-glycerol-water mixture at slightly alkaline pH. Each of the human urinary anti-neoplastic fractions inhibits the growth of human tumor cell lines without affecting normal human diploid cells. Furthermore, the protein fraction inhibits the growth of certain human tumors cells implanted in a nude mouse.

The chemical and biological properties of the extracted and purified antineoplastic peptide fraction isolated from human urine are as follows:

(1) The molecular weight of the peptide is approximately 600 as determined by filtration through Amicon Diaflo membranes.

(2) The peptide is stable to heat at 90° C. for ten minutes.

(3) The antineoplastic activity of the peptide is almost totally destroyed upon treating the dry fraction with either anhydrous methanol or absolute ethyl alcohol. After either of these alcohol treatments the dried fraction is essentially inactive as an antineoplastic agent.

(4) The active peptide fraction shows an Rf value between 0.4–0.6 upon paper chromatography in an n-Butanol: acetic acid: pyridine: water system (30:6:20:24).

(5) The active peptide fraction shows antineoplastic activity against the following human tumor cell lines: breast, melanoma, pancreas, bladder and lung. These antineoplastic activities are measured in vitro by tissue culture techniques.

The chemical and biological properties of the extracted and purified antineoplastic urinary (ANU) protein are as follows:

(1) The molecular weight of the ANU-protein is between 20,000–40,000 daltons.

(2) The ANU-protein contains carbohydrate, is heat stable at 90° C. for twenty minutes, soluble in phenol saturated with water and stable to acid at pH 2 to 4° C. for 48 hours.

(3) The ANU-protein fraction inhibits the growth of the following human tumor cell lines: breast, melanoma, bladder, cervix and lung.

(4) The ANU-protein is non-toxic to human diploid cell lines.

(5) The ANU-protein is a specific antineoplastic agent for human tumor cell lines since neither mouse tumor cell lines nor normal mouse cells are affected by ANU-protein.

(6) The ANU-protein represses the growth and causes regression of human tumor cell lines, for example, the SEP-2 human lung tumor cell lines implanted in the nude mouse.

(7) The ANU-protein does not inhibit human pancreas tumor cell lines PANC/3 or SV-40 transformed WI-38 human lung cells.

(8) The ANU-protein does not exhibit antiviral activity.

In one embodiment of the present invention, Florisil in two mesh sizes, 15–30 mesh and 30–60 mesh, is prepared for adsorption first by flotation removal of the fines, then suspension in dilute ascorbic acid (pH 3–4) at room temperature for several hours before use.

Voided human urine is poured collected in bulk, and boric acid crystals and the butyl ester of p-hydroxybenzoic acid are placed in the containers to prevent bacterial growth. About one liter of the collected urine, at room temperature, is poured through a stack of two jersey fabric bags containing Florisil. The upper bag contains about 0.5 pound of 15–30 mesh Florisil and the lower bag contains about 0.5 pound of 30–60 mesh Florisil. The use of two bags of different mesh Florisil prevents clogging. When voided human urine is collected in situ at a urinal and Florisil granules are carried on a tray as described in Sloane's U.S. Pat. No. 3,711,377, a jersey fabric bag of pellets of boric acid with p-hydroxybenzoic acid butyl ester is placed on top of the two Florisil containing bags.

After the urine has fully contacted the Florisil to permit adsorption of the desired materials, the Florisil is washed with about three liters of cold distilled water (about 4° C.). All subsequent elution and purification procedures are performed at about 2°–4° C.

The antineoplastic peptide fraction is eluted with about 1500 ml cold aqueous acetone (15%) at pH 9–9.5. This fraction is then adjusted to pH 7–7.5 with 2 normal cold HCl and concentrated by removal of acetone in vacuo. The concentrate is purified by passage through an Amicon Diaflo UM2 membrane, which restrains materials having molecular weights greater than about 1,000, then through an Amicon Diaflo UM05 membrane, which restrains materials having molecular weights greater than about 600. This filtered fraction is further purified by standard paper chromatography techniques.

After the peptide fraction has been first eluted, the antineoplastic protein fraction is then eluted from the Florisil by aqueous aceton (15%) containing 30% glycerol at pH 9–9.5. The protein eluate is adjusted to pH 7–7.5 with two normal HCl and then concentrated by filtration through an Amicon Diaflo membrane UM20; which restrains materials having molecular weights in excess of about 20,000. The desired antineoplastic protein does not pass through this membrane. The protein solution is then dialyzed against distilled water and lyophilized. The lyophilized protein is further purified by Sephacryl S-200 chromatography at neutral pH, phosphate buffered at 0.1 molar. The purified antineoplastic protein yield is approximately 300 μg per liter of urine, at a concentration approximately 500 times the concentration in urine. The purified ANU-protein exhibits anti-neoplastic activity at concentrations of less than 1 μg protein per milliliter of medium.

Nude mice experiments were performed in the following manner:

4- to 6-week old NIH athymic (nu/nu) mice were transplanted subcutaneously with human carcinoma cell line HEP 2 ($10^7$ cells/mice). Four days post transplantation separate groups of mice were treated subcutaneously once every 3 days with 1 μg of pure or crude ANU-protein in medium. Control groups received 0.1 ml of medium containing 10% fetal calf serum. Tumor growth was monitored for 3–4 weeks. At the end of this period, tumor volumes were measured and the tissues processed for histology. A minimum of eight mice were used in each group. Additional control groups received ANU-protein alone in medium without tumor transplant. Treatment with crude ANU-protein resulted in a significant reduction in tumor volume (4.1 $cm^3$ to 1.8 $cm^3$ average). Treatment with semi-purified ANU-protein resulted in total regression of tumor in four of eight cases and significant reduction in tumor size in the remaining animals.

In vitro studies were performed in the following manner:

Approximately $10^5$ cells of each cell line under study were inoculated with 5 ml of the medium into cell culture flasks (Falcon #3013 flasks, 25 $cm^2$ area); the protein fractions were dissolved in phosphate buffered saline and added to the cells in the medium. The cultures were incubated at 37° with 5% $CO_2$ for 96–144 hours; control flasks contained additional buffer. At the end of the assay period, the cells were counted after removal from the flask by EDTA-trypsin solution (Gibco).

The ANU-protein inhibited the growth of human breast, melanoma, bladder, cervix and lung tumor cell lines.

While a preferred embodiment has been described hereinabove, it will be recognized that there is no intent to limit the invention by such disclosure, but rather it is intended to cover all modifications and variations falling within the spirit and scope of the invention as defined in the appended claims.

I claim:

1. A method for extracting a glycoprotein fraction including a glycoprotein having a molecular weight of between about 20,000 Daltons and about 40,000 Daltons, said protein exhibiting antineoplastic activity, from human urine containing said glycoprotein fraction, said method comprising contacting a magnesium silicate adsorbent with human urine, washing nonadsorbed urine from said adsorbent, and eluting said glycoprotein fraction from said adsorbent with a mixture of aqueous acetone and glycerol comprising about 15% aqueous acetone containing about 30% glycerol at a pH of between about 8.5 and about 9.5.

2. The method of claim 1 wherein said nonadsorbed urine is washed from said adsorbent with water.

3. The method of claim 1 wherein an antineoplastic peptide fraction is eluted from said adsorbent prior to elution of said glycoprotein fraction.

4. The method of claim 3 wherein said peptide fraction is eluted with aqueous acetone.

5. The method of claim 3 wherein said peptide fraction is eluted with about 15% aqueous acetone at a pH of between about 8.5 and about 9.5.

6. The method of claim 1 wherein said adsorbent comprises granules having a size between about 15 mesh and about 60 mesh.

7. The method of claim 1 wherein said eluted glycoprotein fraction is purified and concentrated by membrane filtration.

8. The method of claim 7 and further comprising dialyzing said fraction against distilled water.

9. The method of claim 8 and further comprising lyophilizing said glycoprotein fraction.

10. The method of claim 1 wherein said silica gel is contacted with said urine at about room temperature.

11. The method of claim 1 wherein said glycoprotein fraction is eluted at a temperature of between about 2° C. and about 4° C.

12. A glycoprotein, having a molecular weight of between about 20,000 Daltons and about 40,000 Daltons extracted from human urine by contacting a magnesium silicate adsorbent with human urine, washing nonadsorbed urine from said adsorbent and eluting said glycoprotein from said adsorbent with a mixture of aqueous acetone and glycerol, comprising about 15% aqueous acetone containing about 30% glycerol at a pH of between about 8.5 and about 9.5, said glycoprotein exhibiting antineoplastic activity in human tumor cell lines.

* * * * *